US00PP21915P3

(12) United States Plant Patent
Hosogai

(10) Patent No.: US PP21,915 P3
(45) Date of Patent: May 10, 2011

(54) **VARIETY OF *ANTIRRHINUM* PLANT NAMED 'ETERNAL'**

(50) Latin Name: *Antirrhinum majus*
Varietal Denomination: Eternal

(76) Inventor: Yohei Hosogai, Niigata (JP)

( * ) Notice: Subject to any disclaimer, the term of this patent is extended or adjusted under 35 U.S.C. 154(b) by 0 days.

(21) Appl. No.: 12/460,516

(22) Filed: Jul. 21, 2009

(65) Prior Publication Data

US 2011/0023199 P1 Jan. 27, 2011

(51) Int. Cl.
*A01H 5/00* (2006.01)

(52) U.S. Cl. ..... Plt./322

(58) Field of Classification Search ..... Plt./263.1, Plt./322

See application file for complete search history.

*Primary Examiner* — June Hwu
*Assistant Examiner* — Louanne C Krawczewicz Myers
(74) *Attorney, Agent, or Firm* — The Webb Law Firm

(57) ABSTRACT

A new and distinct cultivar of *Antirrhinum majus* plant named 'Eternal' having reddish-pink colored flowers, a sweet fragrance, and desirable branching.

1 Drawing Sheet

Botanical classification: *Antirrhinum majus.*
Varietal denomination: 'Eternal'.

BACKGROUND OF THE INVENTION

The present invention comprises a new and distinct cultivar of *Antirrhinum majus* (snapdragon) known by the varietal name 'Eternal'. The new variety was discovered and selected by the breeder in a cultivated environment among plants of *Antirrhinum majus* 'Candy Snap' (unpatented). The new variety was discovered in Niitsu City, Niigata, Japan in 2005 as a naturally-occurring sport of 'Candy Snap'. Asexual reproduction of the new cultivar in Niitsu City, Japan by terminal or axillary cuttings has shown that the unique features of the new variety are stable and reproduced true to type in successive propagations by asexual reproduction.

The new variety has finer foliage variegation than 'Candy Snap', its foliage is more silver-grey in color, and the new variety is more vigorous with better branching than 'Candy Snap'. Further, unlike 'Candy Snap', the new variety has variegated foliage.

Applicant is not aware of any other variegated varieties to use as comparison with 'Eternal' other than 'Candy Snap'.

BRIEF DESCRIPTION OF THE DRAWING

The accompanying colored photographic drawing illustrates the new variety, with the colors being as nearly true as is possible to obtain in colored illustrations of this type.

DESCRIPTION OF THE PLANT

Figure 1:
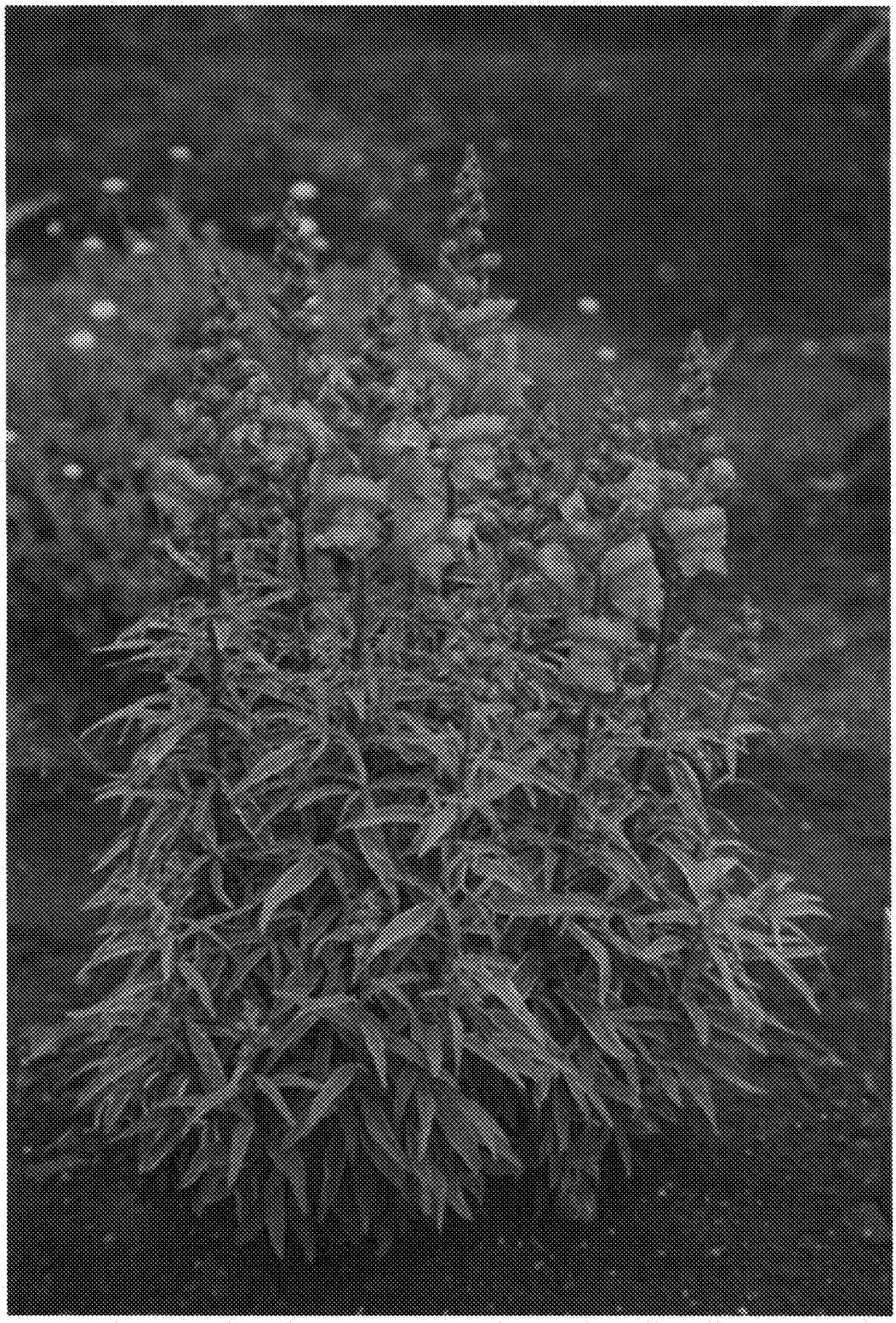
FIG. 1 is a photograph of the entire plant of the new variety.

The cultivar 'Eternal' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, 2001 Edition, except where general terms of ordinary dictionary significance are used. The plants were grown in a field under natural light in Hillegom, The Netherlands. The plants were in full growth during summer conditions and were six months old when described under natural daylight.

PLANT AND FOLIAGE DESCRIPTION

Time to initiate roots: 7-9 days.
Time to develop roots: 12-14 days.
Form: Upright columnar growth.
Height (from soil to top of flowers): Up to a maximum of 60 cm.
Plant diameter: Up to a maximum of 30 cm.
Vigor: Good to very good.
Branching habit: Freely branching with many side shoots.
Lateral branches:
- *Form.*—Upright.
- *Color.*—RHS 147D.
- *Texture.*—Smooth and silky.
- *Length.*—Up to a maximum of 20 cm.
- *Diameter.*—Up to a maximum of 5 mm. (measured 5 cm. from the ground).
- *Internode length.*—Average of 12 mm.
- *Quantity.*—Every leaf axil makes lateral shoots until flower initiation. There are normally 16 to 20 laterals per main shoot.

Foliage:
- *Arrangement.*—Alternate, single.
- *Number of leaves per branch.*—Average of 35.
- *Size of leaf.*—Length: Average of 6.5 cm. Width: Average of 1.4 cm.
- *Shape of leaf (generally).*—Lanceolate.
- *Shape of apex.*—Acute, pointed.
- *Shape of base.*—Acute, pointed.
- *Texture.*—Upper Surface: Slightly uneven. Lower Surface: Smoother than the upper surface with venation present.
- *Aspect.*—Held horizontal, parallel to ground.
- *Margin type.*—Smooth, entire.
- *Color.*—Young leaves: Upper surface: RHS 191A, edged RHS 8D. Lower surface: RHS 194A, edged RHS 8D. Mature leaves: Upper surface: RHS 191A, edged RHS 10D. Lower surface: RHS 191B, edged RHS 10D.

*Petiole.*—Length: Average of 12 mm. Diameter: Average of 2 mm. Color: RHS 139C.

*Veins.*—Venation type: Cross-venulate. Color: Upper surface: RHS 191A. Lower surface: RHS 194B.

FLOWER

Natural flowering season: Flowers can be seen 12 months of the year in favorable conditions, but the main flowering period is from February to July.

Flower type and habit: Flowers are tubular with 5 petals (2 symmetrical dorsal petals, 2 symmetrical lateral petals, and 1 central ventral petal arranged in a zygomorphic form.

Number of flowers per plant: A plant can carry on average 25 flowers per stem and a 6 month old plant can produce 12+ flower stems, resulting in more than 300 flowers per plant.

Time of day of flower opening: Flowers are open all day long.

Bud:

*Stage of development when described.*—Immediately prior to opening.

*Shape.*—Like an oblong box with rounded corners.

*Diameter.*—Approximately 15 mm.

*Length.*—Approximately 28 mm.

*Color.*—Tip of bud: Between RHS 54A and RHS 54B. Mid section of bud: Between RHS 55C to RHS 55B.

Inflorescence:

*Length.*—Up to 15 cm.

*Diameter.*—Approximately 8 cm.

*Type.*—Raceme.

*Habit.*—Stiff and upright.

*Number per stem.*—20-24.

Flower:

*Diameter.*—Approximately 26 mm.

*Average height.*—Typical.

*Flower tube length.*—Average 20 mm.

*Flower tube diameter at distal end.*—Average of 12 mm.

*Flower tube diameter at proximal end.*—Average of 12 mm.

*Petal quantity.*—5 (2 dorsal petals fused standing upright, 3 fused underneath with 2 lateral petals on either side a ventral petal).

*Upper petal lips.*—Length: Approximately 25 mm. Width: Approximately 40 mm. Shape: Two joined segments form a heart shape. Apex: Rounded. Margin: Smooth; entire. Upper & lower surface texture: Smooth and velvety. Upper surface color: 54A. Lower surface color: 55A.

*Lower petal lips.*—Length: Approximately 14 mm. Width: Approximately 16 mm. Apex: Rounded. Margin: Smooth; entire. Upper & lower surface texture: Smooth and velvety. Upper surface color: 54A. Lower surface color: 55A.

Pedicel:

*Length.*—Average of 6 mm.

*Diameter.*—Average of 1.5 mm.

*Color.*—RHS 147D.

*Orientation.*—Upright and parallel to branch.

*Strength.*—Strong.

Sepals:

*Shape.*—Ovate.

*Length.*—Average of 10 mm.

*Diameter.*—Average of 10 mm.

*Shape.*—Goblet-shaped (5 sepals).

*Apex.*—Acute.

*Base.*—Rounded.

*Margin.*—Smooth, entire.

*Upper and lower surface texture.*—Smooth; lightly hirsute.

*Color.*—Upper surface: RHS 147D, edged RHS 10D. Lower surface: RHS 147D, edged RHS 10D.

Disease resistance: No particular susceptibility to diseases observed to date.

Fragrance: Soft and sweet.

Weather tolerance: Good.

Lasting quality:

*On plant.*—Flowers last 7 to 8 days.

*Of cut flowers.*—Not tested.

*Seed production.*—None observed.

REPRODUCTIVE ORGANS

Stamens:

*Number (per flower).*—4 (in 2 pairs).

*Filament length.*—Pair 1: Average of 20 mm. Pair 2: Average of 14 mm.

*Anthers.*—Shape: Like a two-pronged fork with ovate prongs. Length: Average of 2 mm. Color: RHS 9C.

*Pollen.*—Color: RHS 9C. Amount: Little.

Pistil:

*Number.*—1.

*Length.*—Average of 21 mm.

*Styles.*—Length: Average of 18 mm. Color: RHS 55D.

*Stigma.*—Shape: Club-shaped. Color: RHS 10D. Ovary color: RHS 10D.

I claim:

1. A new and distinct *Antirrhinum majus* plant named 'Eternal' as is herein described and illustrated.

* * * * *